(12) United States Patent
Melsheimer (10) Patent No.: US 11,134,951 B2
(45) Date of Patent: Oct. 5, 2021

(54) SIDE-TO-SIDE ANASTOMOSIS SYSTEM AND PUNCH TOOL FOR SAME

(71) Applicant: Cook Medical Technologies LLC, Bloomington, IN (US)

(72) Inventor: Jeffry Scott Melsheimer, Springville, IN (US)

(73) Assignee: Cook Medicol Technologes, LLC, Bloomington, IN (US)

( * ) Notice: Subject to any disclaimer, the term of this patent is extended or adjusted under 35 U.S.C. 154(b) by 208 days.

(21) Appl. No.: 16/360,711

(22) Filed: Mar. 21, 2019

(65) Prior Publication Data

US 2019/0298363 A1    Oct. 3, 2019

Related U.S. Application Data

(60) Provisional application No. 62/650,555, filed on Mar. 30, 2018.

(51) Int. Cl.
*A61B 17/11*    (2006.01)
*A61B 17/3205*    (2006.01)

(52) U.S. Cl.
CPC ........ *A61B 17/11* (2013.01); *A61B 17/32053* (2013.01); *A61B 2017/1107* (2013.01); *A61B 2017/1139* (2013.01)

(58) Field of Classification Search
CPC .... A61B 2017/1139; A61B 2017/1107; A61B 17/32053; A61B 17/11
See application file for complete search history.

(56) References Cited

U.S. PATENT DOCUMENTS

| | | | |
|---|---|---|---|
| 5,868,763 A | 2/1999 | Spence et al. | |
| 5,893,369 A * | 4/1999 | LeMole | A61B 17/11 606/184 |
| 6,080,176 A * | 6/2000 | Young | A61B 17/32053 606/180 |
| 6,565,581 B1 * | 5/2003 | Spence | A61B 17/11 606/153 |
| 6,673,085 B1 * | 1/2004 | Berg | A61B 17/11 606/139 |
| 8,066,723 B2 | 11/2011 | Suyker et al. | |
| 8,690,901 B2 | 4/2014 | Schulze | |
| 2002/0173809 A1 * | 11/2002 | Fleischman | A61B 17/11 606/153 |
| 2004/0068279 A1 * | 4/2004 | Hindrichs | A61B 17/3209 606/153 |
| 2004/0172049 A1 | 9/2004 | Lee | |
| 2006/0111698 A1 | 5/2006 | Kwon | |

(Continued)

FOREIGN PATENT DOCUMENTS

WO    0056228    9/2000

*Primary Examiner* — Darwin P Erezo
*Assistant Examiner* — Brigid K Byrd
(74) *Attorney, Agent, or Firm* — Liell + McNeil (57) ABSTRACT

A method of making a side-to-side anastomosis includes making first and second holes through a first vessel, and second vessel, respectively, by receiving a jaw of a punch tool into exposed ends of the respective vessels, and then moving a punch tool toward the jaw and through the wall of the vessel. The vessels are joined with an elongate eyelet with a passage that matches a shape of the oval first and second holes. The long axes of the oval holes are oriented parallel to a longitudinal axes of the respective vessels.

11 Claims, 6 Drawing Sheets

(56) References Cited

U.S. PATENT DOCUMENTS

2011/0106119 A1 5/2011 Lin et al.
2011/0118765 A1 5/2011 Aguirre
2014/0088623 A1 3/2014 Yevzlin et al.

* cited by examiner

SIDE-TO-SIDE ANASTOMOSIS SYSTEM AND PUNCH TOOL FOR SAME

TECHNICAL FIELD

The present disclosure relates generally to making a side-to-side anastomosis to join two blood vessels, and more particularly to a scalable geometry and standardized strategy that utilizes a punch tool in the creation of a side-to-side anastomoses.

BACKGROUND

When doing reconstructive or transplant surgery, there are often tiny blood vessels that need to be connected to keep the tissues viable. Typically these vessels are hand sutured, or a device such as the Synovis Flow Coupler may be used at the interface between the two vessels. The former is often very difficult and time consuming to hand suture, and the latter may create a large rigid coupling in the middle of the surgical repair.

The present disclosure is directed toward one or more of the problems set forth above.

SUMMARY

A method of making a side-to-side anastomosis includes removing a scrap of tissue to create a first hole through a wall of a first vessel a first distance from an exposed end of the first vessel. The scrap removal includes receiving a jaw of a punch tool into the first vessel through the exposed end, and moving a punch die of the punch tool toward the jaw and through the wall of the first vessel. A scrap of tissue is removed to create a second hole through a wall of a second vessel a second distance from an exposed end of the second vessel. This removal also includes receiving the jaw of the punch tool into the second vessel through the exposed end, and moving the punch die of the punch tool toward the jaw and through the wall of the second vessel. The first vessel is joined to the second vessel with an elongate eyelet that extends through the first hole and the second hole and urges the first vessel and second vessel into side-to-side contact in a perimeter surrounding the first hole and the second hole, respectively. The first and the second hole have identically sized non-circular elongate shapes with long axes oriented parallel to a longitudinal axis of the first vessel and second vessel respectively. The elongate eyelet defines a passage therethrough with a shape that matches the non-circular elongate shape of the first hole and the second hole.

In another aspect, a side-to-side anastomosis punch tool includes a punch die that moves toward a punch plate responsive to relative movement of a first handle and a second handle. The punch die is attached to a first jaw, and a punch plate is part of a second jaw. A cross sectional shape of the second jaw at the punch plate is different from a die shape of a cutting area defined by the punch die. An area of the cross sectional shape of the second jaw is about equal to an area of an oval that matches the cutting area of the punch die.

DETAILED DESCRIPTION

The present disclosure is directed to a strategy, method, and tool for creating a side-to-side anastomosis that is scalable from micro vascular surgery up to the larger vessels and passageways within a patient's body. The strategy utilizes a punch tool that prepares the two vessel ends in a predictable way for the procedure. The strategy does not rely on specialized user-training or techniques to form the anastomosis consistently. Instead, the strategy utilizes an elongate eyelet to hold the two vessels together in a side-to-side orientation to create the anastomosis, which allows utilization of proven, existing strategies (e.g., clips) to close vessel ends. This strategy also has the ability to accommodate virtually any foreseeable size discrepancy between the two vessels being joined. The strategy also teaches sizing the anastomosis and elongate outlet so that the passageway connecting the two vessels has a cross sectional area about equal to the smaller of the two vessels to be joined. The strategy of the present disclosure also contemplates eyelets that change between a low profile delivery configuration to an attachment configuration either through resilient shape memory or by plastic deformation using a separate crimping tool.

Figure 1:
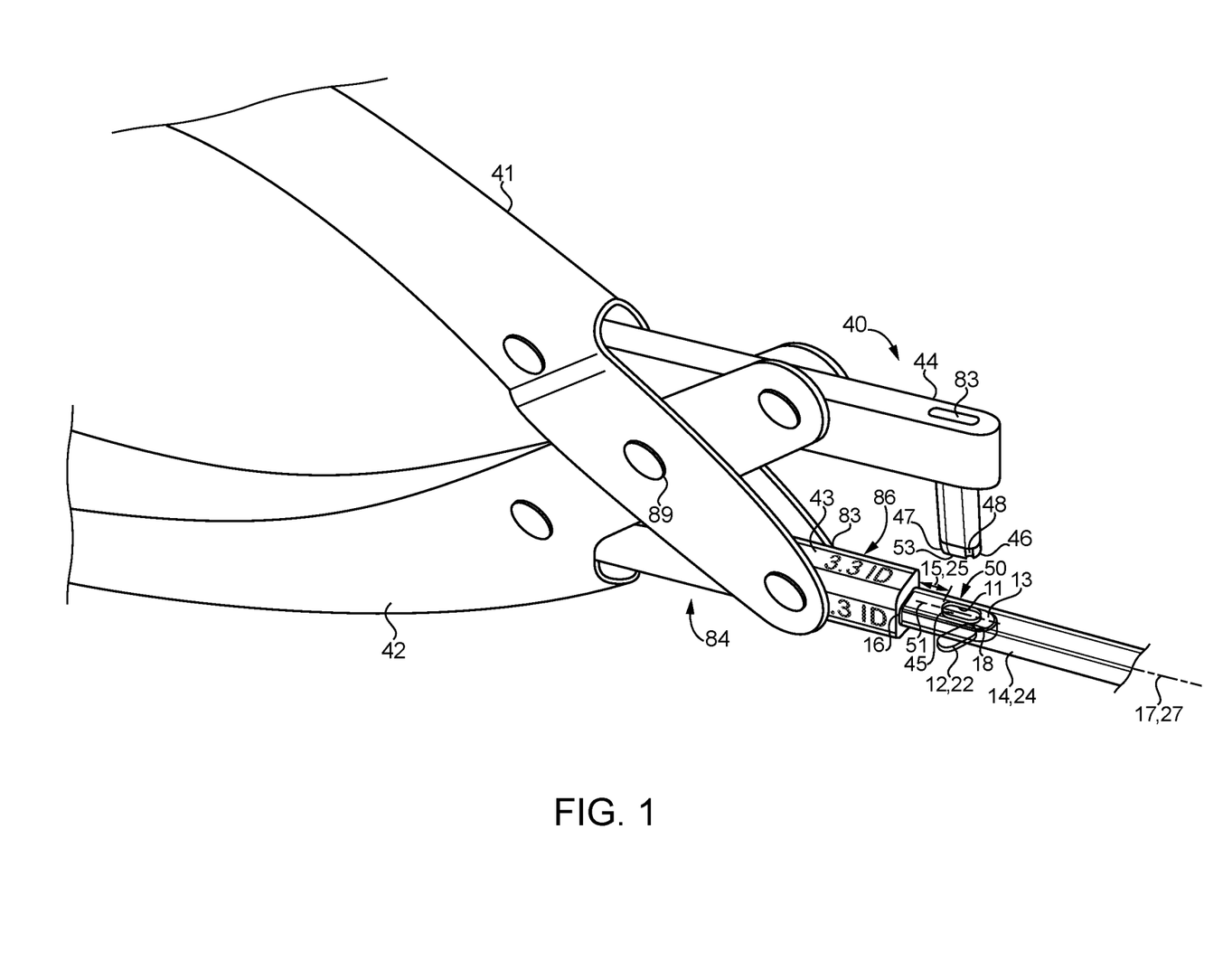
FIG. 1 is a perspective schematic view of a punch tool immediately after punching a hole through a wall of a vessel to be joined in a side-to-side anastomosis.
Figure 15:
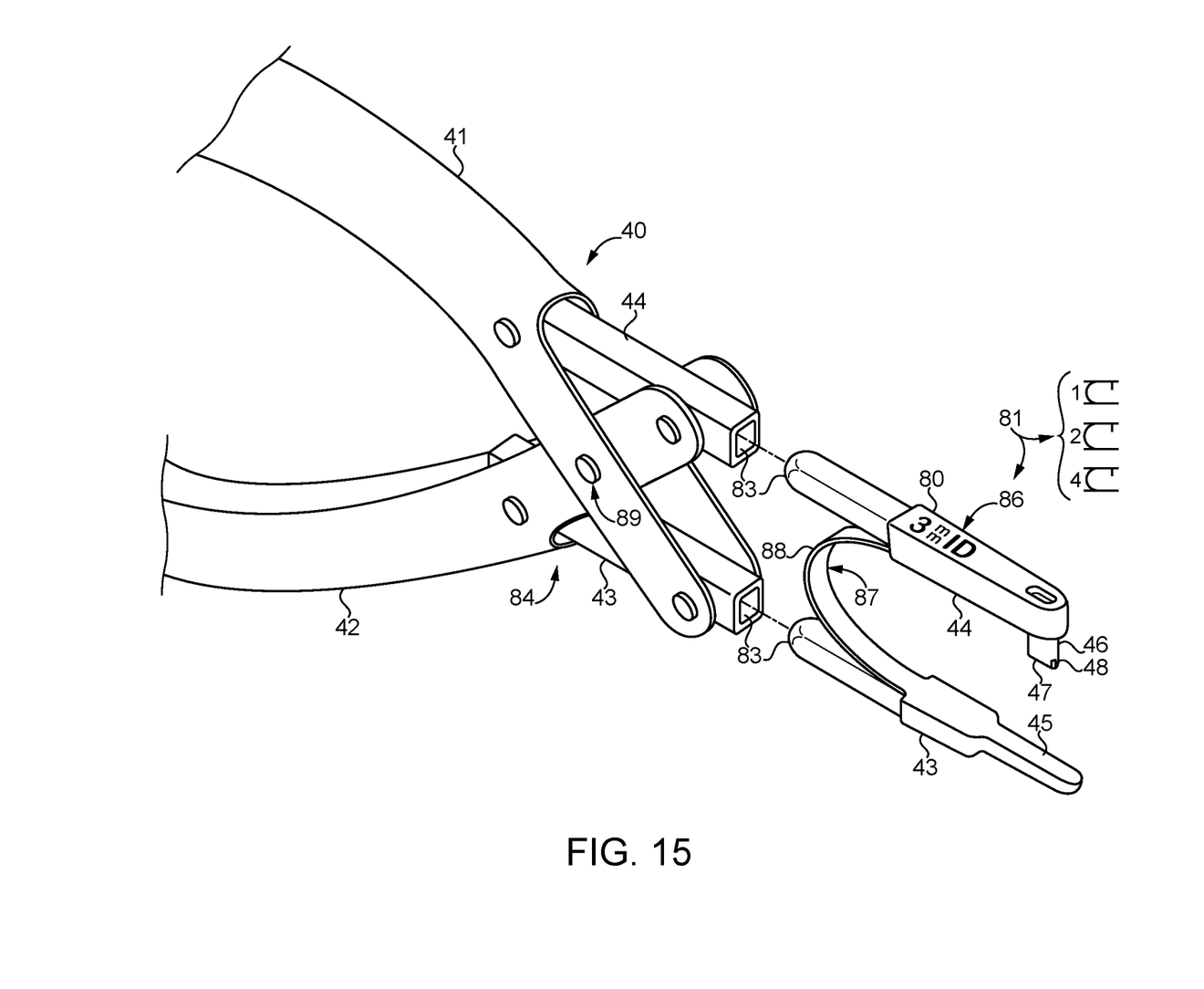
FIG. 15 is a perspective exploded view of a punch tool with one size combination of a plurality of size combinations.

Referring initially to FIGS. 1 and 15, a punch tool 40 according to the present disclosure may have the ability to mate with a plurality of different size combinations 81 in order to accommodate the broad continuum of different sized vessels to be joined. Although one could inventory a plurality of different punch tools that individually have different sized punch die and punch plate combinations, the present disclosure preferably teaches a single punch tool 40 that can mate with any size combination 80 from a plurality of size combinations 81, which might be inventoried. Each size combination 80 includes a punch die 46 shaped to make an oval hole with a cross sectional area that is about equal to an area of the smaller of the two vessels to be joined. Each size combination 80 also includes a second jaw 44 with a cross sectional shape that includes a flat punch plate 45 for contacting the punch die 46, and a cross sectional shape also with an area about equal to the cross sectional area of the smaller of the two vessels. Thus, each size combination 80 includes a jaw sized to be received through an open end of the smaller of the two vessels to be joined and a punch die 46 sized and oriented to make an oval hole through the side of the vessel such that the major axis of the hole is parallel to the longitudinal axis of the vessel.

In order to accommodate a plurality of sized combinations 81, the first and second handles, 41, 42 of the punch tool 40 may include mating features 83 compatible with attachment to each of the plurality of different size combinations 81, which may be inventoried. Each punch die and punch plate size combination 80 may include size indicator markings 86 so that each is marked with a size indicator corresponding to a vessel internal diameter. In the case of the size combinations 81 and shown in FIG. 15, the punch die 46 is connected to the second jaw 44 by an attachment 87 that may serve not only to keep the die and plate combinations together but also include a resilient member 89 that biases the punch die 46 away from contact with the punch plate 45 of second jaw 44. Although not necessary, the punch tools 40 disclosed in FIGS. 1 and 15 include straight line motion linkages 84 so that the punch tie 46 moves perpendicular to the plane 49 defined by punch plate 45 when creating the hole 11 through the wall 13 of the vessel 14. Even with straight line motion linkage 84, handles 41 and 42 can still be thought of as being attached to one another by a pivot 89. Although FIG. 15 shows a size combination 80 with the punch die 46 attached to the second jaw 44 to define size combination, FIG. 1 shows an alternative strategy in which the punch die 46 is unattached to its counterpart second jaw 43. In all cases, each size combination 80 is detachable from the first and second handles 41, 42, but alternate strategies would also fall within the intended scope of the present disclosure.

A punch tool 40 according to the present disclosure includes a punch die 46 that moves toward a punch plate 45 responsive to relative movement of a first handle 41 and a second handle 42. The punch die 46 is attached to a first jaw 43, and the punch plate 45 is part of a second jaw 44. Preferably, that attachment is a removable attachment in order to allow the handles 41, 42 to mate with a variety of different sized punch die/punch plate size combinations 81. As shown in FIG. 1, the second jaw 44 of punch tool 40 is received through the exposed end 16 of a first vessel 14. Preferably, the first vessel 14 is received on jaw 44 until its exposed end 16 contacts an abutment surface in order to establish a predetermined first distance 15 from the exposed end 16 for forming a first hole 11 through a wall 13 of first vessel 14. The punch die 46 includes a cutting edge 47. While a cutting edge 47 that defined a closed perimeter would fall within the scope of the present disclosure, it may be preferable for cutting edge 47 to have an unclosed perimeter 53 of the oval hole 11 so that the punch die 46 produces a chad 12 that has a shape that matches the oval hole 11. With this strategy, the individual chad or scrap tissue 12 can avoid becoming lost by providing the clinician with the control over finally detaching the scrap 12 with forceps or the like in order to account for the removed tissue in a controlled manner. The punch die 46 may define a notch 48 so that the line of cutting edge 47 defines an unclosed perimeter 53 so that the punch die produces a hanging chad 12. In this way, the scrap 12 or chad remains attached to vessel 14 at chad attachment 18 for later removal at a timing chosen by the clinician.

Figure 2:
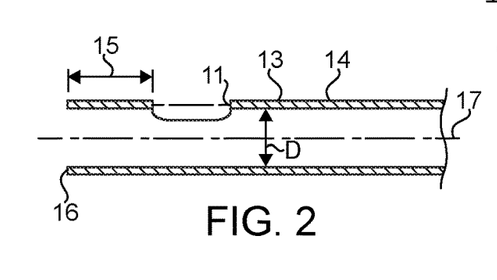
FIG. 2 shows a schematic sectioned side view of the vessel of FIG. 1 after being separated from the punch tool.
Figure 3:
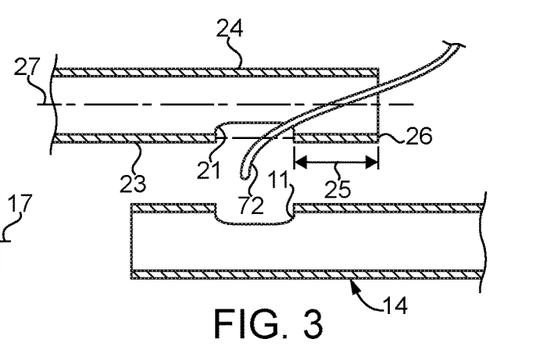
FIG. 3 shows an initial step in joining the first vessel to a second vessel to create a side-to-side anastomosis.
Figure 4:
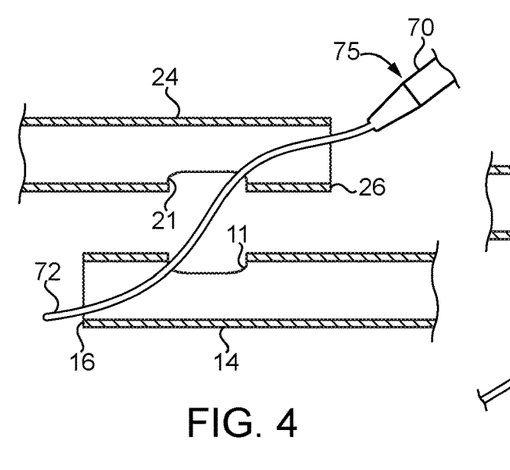
FIG. 4 is a further step in the process after a wire guide has been received through the exposed end of the first vessel, through the first hole, the second hole, and then out of the exposed end of the second vessel.

Although the two vessels may be different in size, preferably both vessels are punched with the die/plate size combination 80 that corresponds to the smaller of the two vessels. FIG. 1 shows the situation immediately after punch die 46 of punch tool 40 has moved toward lower jaw 44 and through the wall 13 of vessel 14 to create oval shaped hole 11, while the scrap of tissue 12 hangs as a chad at chad attachment 18. Referring now in addition to FIGS. 2-7, after first vessel 14 has been prepared as shown in FIG. 2, the second vessel is prepared by receiving the jaw 44 of the punch tool 40 through the exposed end 26 of the second vessel 24 to create a second hole 21. This process likewise produces a scrap or chad of tissue 22 which is shown still attached in FIG. 1, but after being removed in FIG. 3. Like the first vessel 14, the punch die 46 of the punch tool 40 moves toward the jaw 44 and through the wall 23 of the second vessel 24 to create the second hole 21 a second distance 25 from the exposed end 26 of the second vessel 24. Because the same punch die 46 is used, both the first hole 11 and the second hole 21 have the same oval shape, and both have the major axis or long axis 51 oriented in parallel to the respective longitudinal axis 17, 27 of the first vessel 14 and the second vessel 24. In addition, these ovals have a cross sectional area about equal to a cross sectional area of the smaller of the two vessels 14. As used in the present disclosure, the term "about equal" means that the ratios of the two areas when taken to a single significant digit is the numeral one. After the first scrap 12 of tissue has been removed from first vessel 14 and the second chad or scrap of tissue 22 has been removed from second vessel 24, the two vessels may be arranged in parallel as shown in FIG. 3 with their respective exposed ends 16 and 26 pointing in opposite directions.

Figure 5:
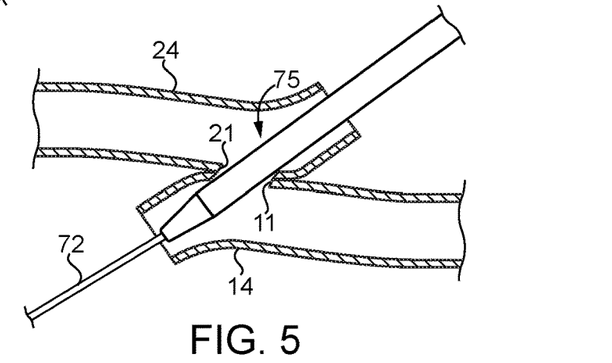
FIG. 5 shows a later step in the process where a delivery device has been moved along the wire guide and through the holes separating the two vessel passages.
Figure 6:
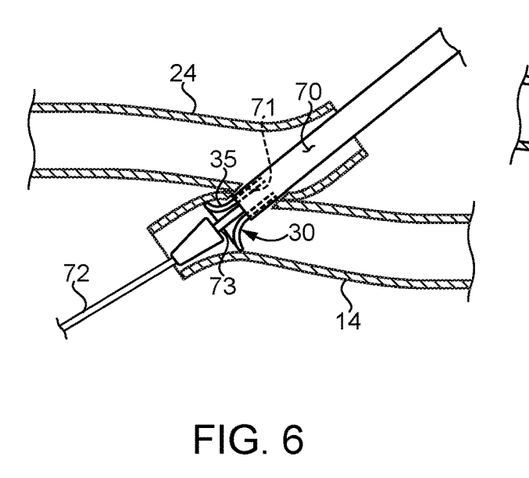
FIG. 6 is a further step in the process showing an elongate eyelet being partially deployed by the delivery device in the holes.
Figure 7:
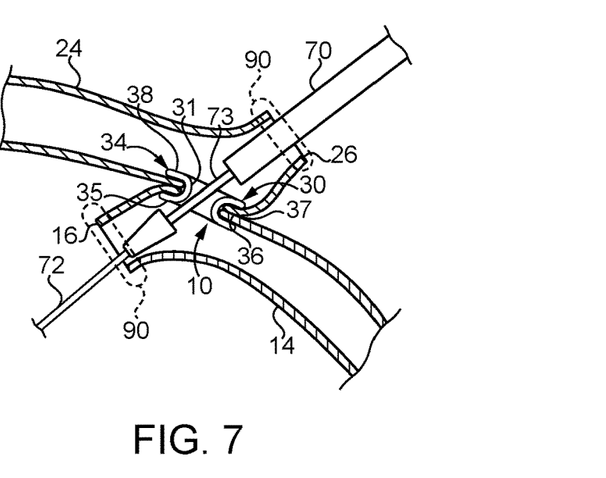
FIG. 7 shows the delivery device still positioned in the vessels but after the elongate eyelet has been deployed to join the first vessel to the second vessel at a side-to-side anastomosis.
Figure 8:
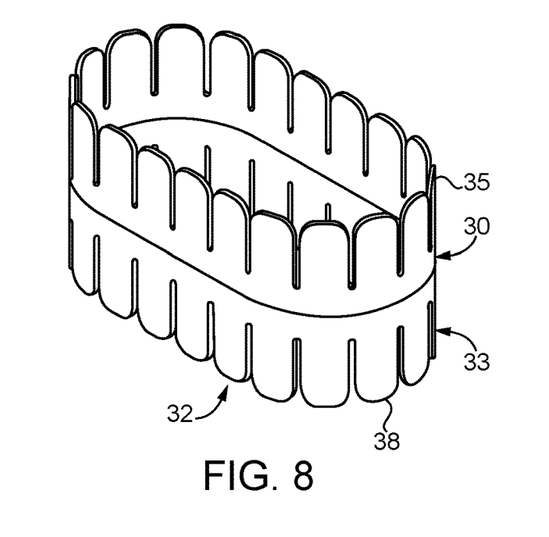
FIG. 8 is a perspective schematic view of an elongate eyelet for joining two vessels in a side-to-side anastomosis.
Figure 9:
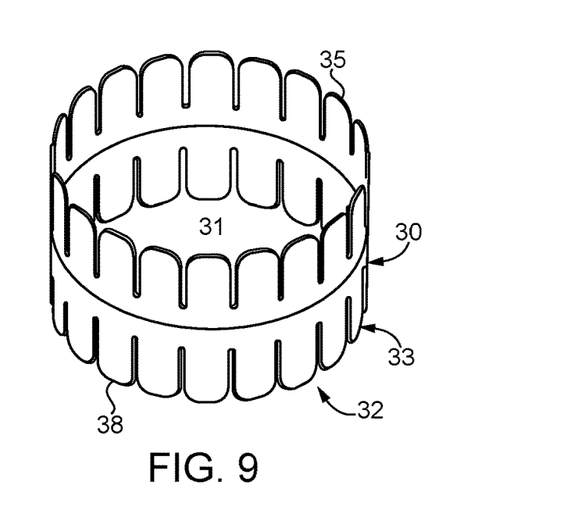
FIG. 9 shows the elongate eyelet of FIG. 8 elastically deformed into a circular shape.

After arranging the vessels as shown in FIG. 3, a wire guide 72 may be passed through the exposed opening 26 of the second vessel 24 out through oval hole 21 into oval hole 11 and out through the exposed end 16 of the first vessel 14. Next, a delivery device 75 which includes a sheath 74 constraining an elongate eyelet 30 in a delivery configuration with an inner surface 71 of the sheath 70. When the sheath 70 is properly positioned, as shown in FIG. 5, the sheath 70 may be withdrawn to allow the elongate eyelet 30 to resiliently transform from its delivery configuration 33 constrained within sheath 70 to its attachment configuration 34 as shown in FIG. 7. In the attachment configuration 34 the elongate eyelet 30 extends through the first hole 11 and the second hole 11 and urges the first vessel 14 and the second vessel 24 into side-to-side contact 36 in a perimeter 37 surrounding the first hole 11 and the second hole 21, respectively. In particular, eyelet 31 may include first grippers 35 that contact the inner surface of vessel 14 at a perimeter surrounding first hole 11, and a second set of grippers 38 that contact the inner surface of second vessel 24 in a perimeter surrounding second hole 21. Thus in this resilient strategy, the shape 32 of the elongate eyelet 30 changes away from the delivery configuration (not visible but constrained within sheath 70) toward the attachment configuration 34 by moving the sheath 70 out of contact with the elongate eyelet 30. As stated earlier, the passage 31 defined by elongate eyelet 30 has a cross sectional area about equal to an area of the smaller one of the two vessels 14, 24.

After the elongate eyelet 30 has been delivered as shown in FIG. 7, the delivery device 75 and wire guide 72 may be withdrawn so that the exposed ends 16 and 26 of the first and second vessels 14, 24 can be closed, such as with ordinary proven existing clips 90. However, prior to permanently closing exposed ends 16 and 26, they may be held closed, such as with an appropriate clamp to test the side-to-side anastomosis 10 against leakage and/or other problems that could be remedied at the time. If the clinician is satisfied with the side-to-side anastomosis 10, the exposed ends 16 and 26 may be closed with an appropriate proven existing clip 90 in a manner well known in the art. The delivery device 75, in addition to sheath 70, may include an inner catheter 73 that terminates in a dilator end to facilitate transition from the wire guide diameter to the outer diameter of sheath 70. The elongate eyelet 30 may be mounted about the inner catheter 73 but constrained by the inner wall surface 71 of sheath 70. Nevertheless, those skilled in the art will appreciate that other ways of constraining an elongate eyelet and positioning the same for attachment to the two vessels 14 and 24 would also fall within the intended scope of the present disclosure.

Figure 10:
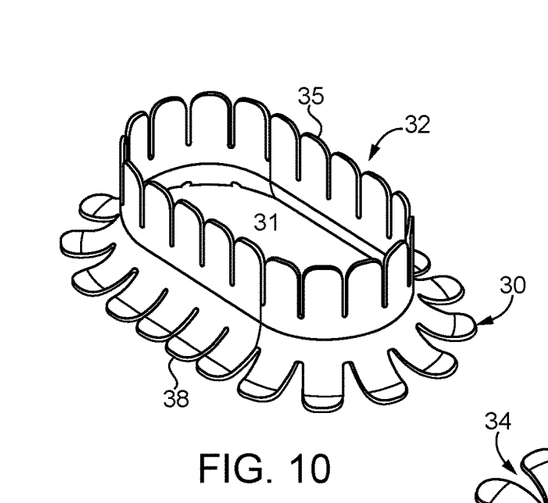
FIG. 10 is a schematic perspective view of the eyelet of FIG. 8 after a first set of grippers have changed the shape of the eyelet from a delivery configuration toward an attachment configuration.
Figure 11:
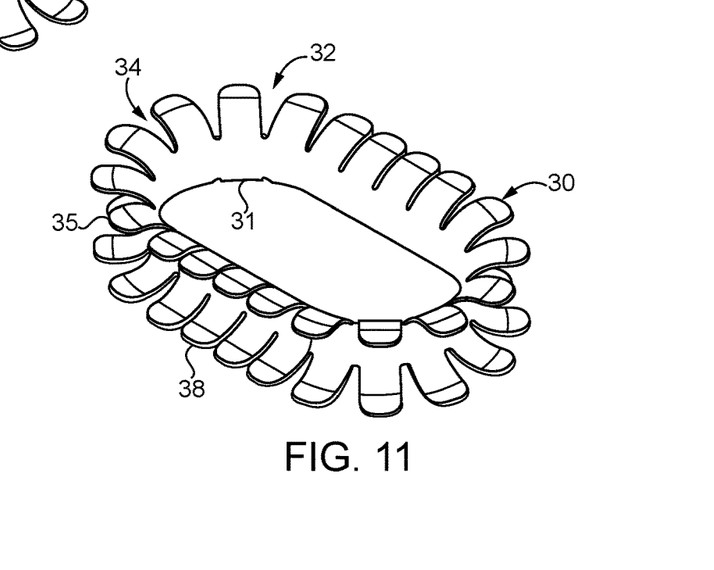
FIG. 11 shows the eyelet of FIG. 8 after both the first and second set of grippers have deformed to place the elongate eyelet in its attachment configuration.

Referring now to FIGS. 8-11, an example elongate eyelet 30 according to the present disclosure is illustrated. The elongate eyelet 30 may or may not include a closed band that straddles the space where the two vessels contact one another, or may rely upon the vessel contact to close the passageway for the anastomosis 10. The elongate eyelet is shown as including multiple individual grippers 35, 38 that deform to grip the inner surface of the respective vessel. Each of the individual grippers 35, 38 has rounded ends but a base attached to the closed core ring of the elongate eyelet 30. The present disclosure also contemplates sharp-ended grippers, which may be preferred in some applications. The elongate eyelet may be made from a suitable shape memory metallic material, such as nitinol, and be configured to have a rest shape associated with a delivery configuration shown in FIG. 11, but be able to be stressed toward the configuration of FIGS. 8 and 9 for corresponding to a delivery configuration 33. The elongate eyelet 30 may be constrained in a delivery configuration in any suitable manner, such as by a sheath 70 as discussed earlier. FIG. 10 corresponds to elongate eyelet being partially deployed as in FIG. 6. Those skilled in the art will appreciate that elongate eyelet 30 can take on numerous different shapes and be made from different materials, including possibly suitable plastics without departing from the present disclosure. In addition, many of the different strategies associated with stent construction technology would also apply to the present disclosure. For instance, elongate eyelets 30 according to the present disclosure could be constructed from bent wire or could be cannula cut without departing from the present disclosure.

Figure 12:
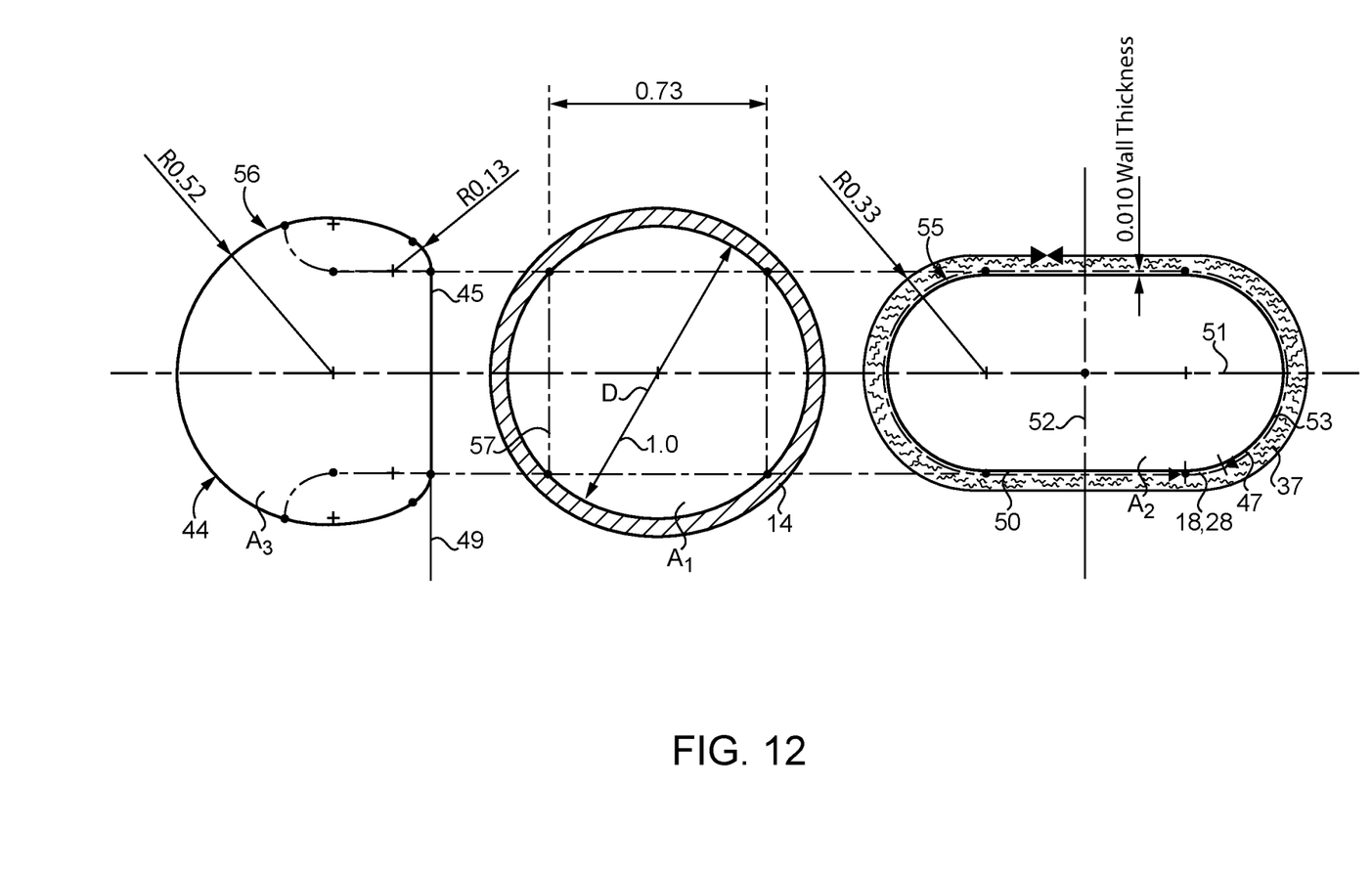
FIG. 12 is a scale illustration of the geometrical relationship between the smaller of the two vessels to be joined and the respective shapes of the punch tool jaw and punch die shape, with the vessel diameter being standardized as 1.000 for scaling.

The passage 31 through the elongate eyelet 30 has a shape that matches the non-circular elongate shapes (ovals) of the first hole 11 and the second hole 21. Referring now to FIG. 12, a to-scale illustration shows an example sizing of various radii, widths and lengths and other dimensions relative to a cross sectional area A1 of the smaller of the two vessels to be joined. In this illustration, the diameter D of the smaller vessel 14 to be joined as standardized to 1.0. To the right, a cross sectional area of the cutting edge line 47 of the punch die 46 is shown to define an oval shape 50 with an unclosed perimeter 53 that would leave behind an uncut edge at chad attachment 18, 28. The elongate oval shape 50 includes a long axis 51 that is oriented parallel to the longitudinal axis 17, 27 of the respective first and second vessels 14, 24. In this example, the elongate shape 50 also has a minor axis 52 that is sized to be equal to a square shape 57 that would fit inside of the vessel 14 as shown with the dashed lines. With this assumption, that yields radii at opposite ends of the oval of 0.3. The end result is an area A2 for the oval shape 50 that is about equal to the cross sectional area A1 of the smaller vessel. The area A2 also corresponds to the area of the passage 31 through the elongate eyelet. The area A2 also corresponds to the die shape 55 for the punch die 46 for this given example. This strategy allows the passage of the side-to-side anastomosis 10 to have a flow area that does not cause a flow restriction because it has a flow area about equal to the flow area A1 of the smaller vessel 14. To the left in FIG. 12, the cross sectional shape 56 of the second jaw 44 of punch tool 40 is shown. Preferably, the cross sectional shape 56 has an area A3 that is again about equal to the area A1 of the smaller vessel 14 to fill the open area of the vessel when received onto jaw 44 as shown in FIG. 1. However, the cross sectional shape 56 includes a flat plane 49 that defines punch plate 45 that the punch die 46 comes in contact with when punching through the vessel wall 13. The width of the flat area is also set to be about equal to the width of one side of the square 57 inscribed in the small vessel 14. This may yield a shape that has a bulk radius of 0.5 and a small radius at the edges of the punch plate 45 of 0.13. Recalling that, all of these are standardized to the small vessel having a diameter of 1.0, yielding a square side edge of 0.73. Thus, those skilled in the art will appreciate that FIG. 12 can be used to scale up the appropriate sizing for the shape of the jaw 44 and the punch die 46 for any given sized vessel. Those skilled in the art will appreciate that FIG. 12 represents just one family of shapes that would fall within the scope of the present disclosure. For instance, oval 50 could have end radii of 0.25 accompanied by a longer long axis 51 to produce an identical area $A_2$, which would still fall within the intended scope of the present disclosure. In such a case, the cross sectional shape 56 of the punch tool jaw could be adjusted accordingly because the punch plate 45 could be made thinner to reflect the smaller minor axis 52 of the more elongated oval. Thus, the jaw should have a punch plate 45 to accommodate the minor axis of the oval 50, but in all instances the areas $A_1$, $A_2$ and $A_3$ will be about equal. In the context of the present disclosure, about equal areas means that a ratio of any two of the areas when rounded to one significant digit will be the numeral one. FIG. 12 shows that in a preferred embodiment, the cross sectional area $A_3$ of the jaw 44 of punch tool 40, the cutting area $A_2$ of the die shape 55 defined by the punch die 46, and the cross sectional area A1 of the smaller one 14 have about equal areas A1, A2, A3, but three different shapes. The diameter D of the smaller of the first vessel 14 and second vessel 24 is larger than the minor axis 52 of the oval shape 50, but smaller than the long axis 51.

Figure 13:
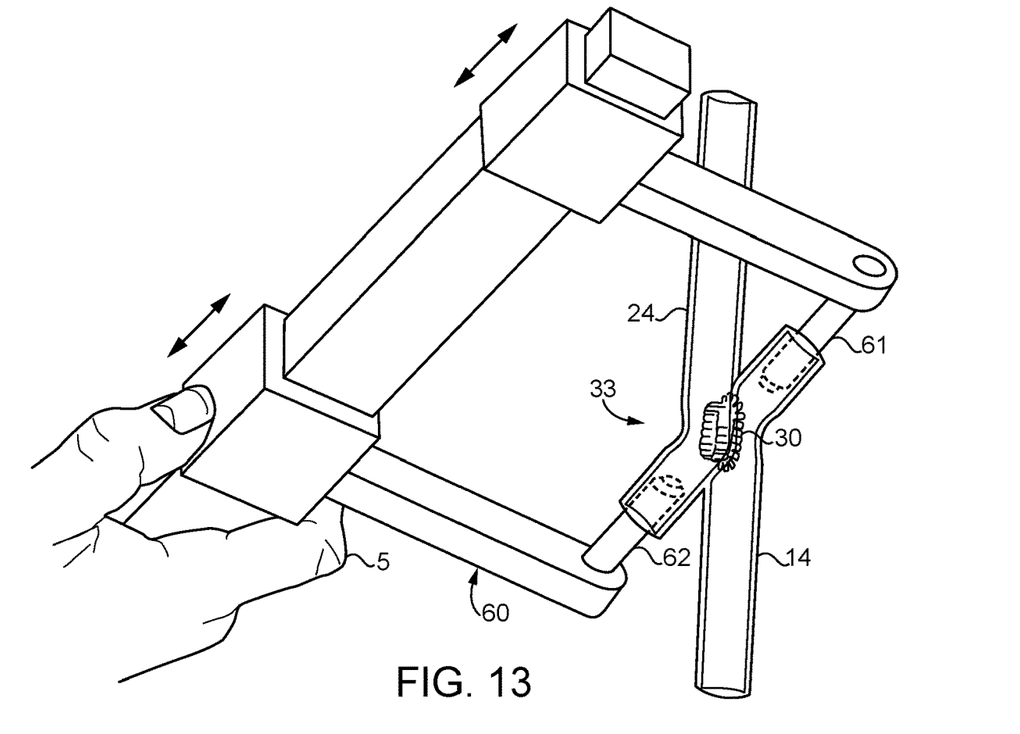
FIG. 13 is a schematic perspective view of a crimp tool being used to deform an elongate eyelet during the attachment of the first vessel to a second vessel according to another aspect of the present disclosure.
Figure 14:
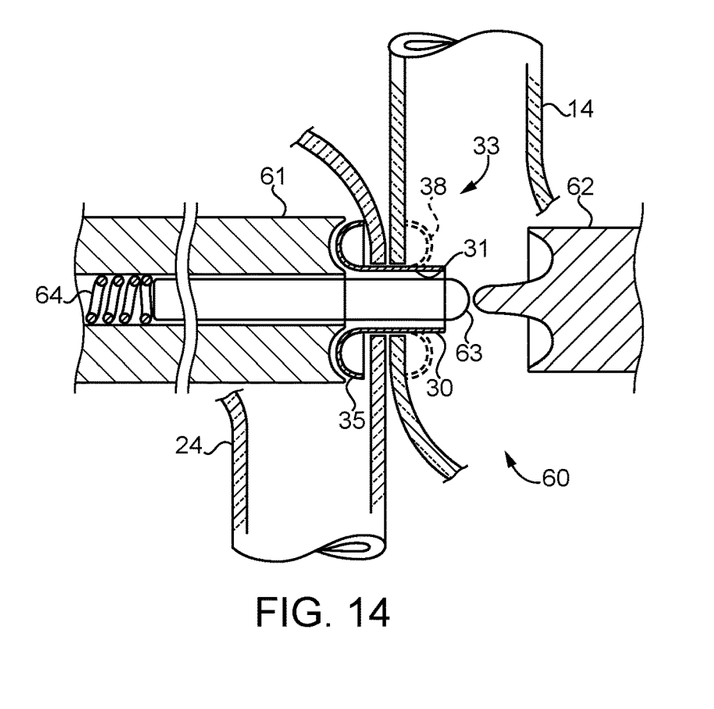
FIG. 14 is a schematic enlarged sectioned side view of the crimp tool being used to deform an elongate eyelet to join the first and second vessels.

Referring now to FIGS. 13 and 14, an alternative strategy of the present disclosure teaches an elongate eyelet 30 that is plastically deformed in situ using a crimp tool 60. In this strategy, after the vessels have been prepared with the punch tool 40 as previously described, the elongate eyelet 30 may be mounted on a crimping tool 60 with one of side grippers 35 already formed as shown in FIG. 14. In other words, elongate eyelet 30 may be mounted on a first mandrel 61 around a centering piece 63 that is received through the passageway 31 defined by the elongate eyelet. Next, the crimping tool is actuated to move mandrel 61 toward mandrel 62 to deform the second set of side grippers 38 into contact with the inner surface of the first vessel as shown by the dotted lines in FIG. 14. In this embodiment, the centering piece 63 associated with mandrel 61 may be spring biased with a spring 64. Nevertheless, those skilled in the art will appreciate that numerous differently shaped and operated crimping tools could be used with the present disclosure. A key feature being that the respective mandrels 61, must be sized to slide through the exposed ends 16, 26 of the vessels to be joined 14, 24 in order to plastically deform the elongate eyelet from a delivery configuration 33 to an attachment configuration 34.

INDUSTRIAL APPLICABILITY

The present disclosure is applicable to any situation where there is a desire to join two vessels with exposed ends in a side-to-side anastomosis. The present disclosure finds specific applicability to joining tiny blood vessels associated with reconstructive or transplant surgery. Finally, the present disclosure is applicable to a strategy for joining different sized vessels in a manner that avoids restricting flow through the anastomosis and vessels after the joining is completed.

According to the present disclosure the process is initiated by measuring the cross sectional diameter D and determining the cross sectional area $A_1$ of the smaller of the two vessels to be joined. With this information, one can utilize the scaled drawing of FIG. 12 to determine a sized combination of a punch die 46 and jaw 44 that matches the diameter D of the small vessel 14 to be joined. That size combination 80 of punch die 46 and jaw 44 are then assembled and mated to the punch tool 40 to complete the assembly of punch tool 40 to that specific application. Next, the exposed end 16 of the smaller vessel 14 receives jaw 44 of punch tool 40, and then the punch die 46 of the punch tool 40 is moved toward the jaw 44 and through the wall 13 of vessel 14 into contact with the jaw 44. This process yields a scrap of tissue 12 that may remain attached to the vessel 14 as a hanging chad if the punch die has an unclosed perimeter 53, or may be completely removed if the die has a closed perimeter. After preparing the first vessel 14, the same combination of punch die and jaw are used for creating a second hole 21 in the second vessel 24. In particular, the jaw 44 of the punch tool 40 is received through the exposed end 26 of the second vessel 24, and the punch die 46 is moved toward the jaw 44, through the wall 23 of the second vessel 24 and eventually into contact with the jaw 44. The first vessel 14 and the second vessel 24 are joined with an elongate eyelet 30 that extends through the first hole 11 and the second hole 21, and urges the first vessel 14 and the second vessel 24 into side-to-side contact 36 in a perimeter 37 surrounding the first hole 11 and the second hole 21, respectively.

As discussed earlier, the shape of the elongate eyelet 30 may be transformed from a delivery configuration 33 to an attachment configuration 34 either resiliently and/or through plastic deformation, or partially both. By utilizing the teachings of the present disclosure, the first hole 11 and the second hole 21 will have identically sized non-circular elongate shapes 50 with long axes 51 oriented parallel to the respective longitudinal axis 17 and 27 of the first and second vessels 14, 24. Furthermore, the elongate eyelet 30 will define a passage 31 therethrough with a shape that matches the oval non-circular elongate shape 50 of the first hole 11 and the second hole 21.

The punch tool 40 and the introducing tool (e.g., delivery device 75 or crimping tool 60) could be formed and manufactured in typical fashion from medical grade materials. In one specific example, the elongate eyelet 30 could be laser cut from a tube of nickel/titanium alloy, and have cuts forming slots and/or perforations which produce the gripping fingers 35 and 38 that lend flareability to the eyelet. The laser/cut tube may then be stressed relieved, passivized, electro polished and inspected. The elongate eyelet 30 may then be carefully formed and heat treated to give the shape memory necessary to move from a delivery configuration 33 to an attachment configuration 34 during a phase change. In an alternative embodiment, the elongate eyelet might be laser cut from stainless steel and flared during manufacturing, with the second set of grippers 38 flared in the body (FIG. 14) using the crimping tool 60, instead of the delivery device 75 of the other embodiment.

In summary, a first vessel and a second vessel are measured for inside diameter and appropriate overlap. An appropriate combination of punch die 46 and jaw size 44 are chosen, and a matching elongate eyelet 30 are selected according to the size of the smaller of the two vessels. The first vessel 14 is pulled onto the lower jaw of the punch tool 40. The punch tool 40 is then actuated to cut the elongate oval hole 11 in the vessel wall 13, and the vessel 14 is then removed from the punch tool 40. This step is repeated for the second vessel 24, insuring that the holes are punched in faces of the vessels 14, 24 will be adjacent to one another. The elongate eyelet 30 then may be loaded onto the appropriate introducing tool (75, 60) through the exposed ends of exposed ends 16, 26 of the vessels 14, 24. The introducer is then actuated to change the elongate eyelet 30 from the delivery configuration 33 to the attachment configuration 34 and the introducer tool (75, 60) is then removed. Thereafter, the ends 16, 26 of the vessels 14, 24 may be temporarily clamped while the repair is checked for leaks. If the anastomosis passes the leak check, the exposed ends 16, 26 of the vessels may be permanently closed with clips, sutures, or glued with an appropriate adhesive.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. A method of making a side-to-side anastomosis, comprising the steps of:

removing a scrap of tissue to create a first hole through a wall of a first vessel a first distance from an exposed end of the first vessel, including receiving a jaw of a punch tool into the first vessel through the exposed end, and moving a punch die of the punch tool toward the jaw and through the wall of the first vessel;

removing a scrap of tissue to create a second hole through a wall of a second vessel a second distance from an exposed end of the second vessel, including receiving the jaw of the punch tool into the second vessel through the exposed end, and moving the punch die of the punch tool toward the jaw and through the wall of the second vessel;

joining the first vessel to the second vessel with an elongate eyelet that extends through the first hole and the second hole and urges the first vessel and second vessel into side-to-side contact in a perimeter surrounding the first hole and the second hole, respectively;

wherein the first hole and the second hole have identically sized non-circular elongate shapes with long axes oriented parallel to a longitudinal axis of the respective first vessel and second vessel;

wherein the elongate eyelet defines a passage therethrough with a shape that matches the non-circular elongate shapes of the first hole and the second hole; and wherein the removing steps are performed before the joining step.

2. The method of claim 1 wherein the passage has a cross sectional area about equal to a cross sectional area of a smaller one of the first vessel and the second vessel.

3. The method of claim 1 wherein the removing steps include punching through the wall of the respective first vessel and second vessel by contacting the punch die with a punch plate of the jaw.

4. The method of claim 3 wherein the punch die contacts the punch plate in a plane.

5. The method of claim 4 wherein the punch die contacts the punch plate along a line that defines an unclosed perimeter of the respective first hole and second hole.

6. The method of claim 3 wherein the punching step is performed with an unclosed perimeter to result in the respective scrap remaining attached to the respective vessel as a first chad and a second chad; and the removing steps includes detaching the first chad from the first vessel, and detaching the second chad from the second vessel, respectively.

7. The method of claim 3 wherein the joining step includes changing a shape of the elongate eyelet from a delivery configuration to an attachment configuration.

8. The method of claim 7 wherein the joining step includes crimping the elongate eyelet with a crimping tool in contact with the eyelet.

9. The method of claim 7 including constraining the elongate eyelet in the delivery configuration with an inner surface of a sheath in contact with the elongate eyelet; and changing a shape of the elongate eyelet away from the delivery configuration toward the attachment configuration by moving the sheath out of contact with the elongate eyelet.

10. The method of claim 1 wherein a cross sectional area of the jaw of the punch tool, a die shape of a cutting area defined by the punch die, and a cross sectional area of a smaller one of the first vessel and the second vessel, have about equal areas and three different shapes.

11. The method of claim 1 including a step of selecting a punch die and jaw size combination, from a plurality of size combinations, based upon a diameter of a smaller one of the first vessel and the second vessel; and assembling the punch tool by mating the selected punch die and jaw size combination with a handle generic to the plurality of size combinations.

* * * * *

UNITED STATES PATENT AND TRADEMARK OFFICE
CERTIFICATE OF CORRECTION

| | |
|---|---|
| PATENT NO. | : 11,134,951 B2 |
| APPLICATION NO. | : 16/360711 |
| DATED | : October 5, 2021 |
| INVENTOR(S) | : Melsheimer |

It is certified that error appears in the above-identified patent and that said Letters Patent is hereby corrected as shown below:

On the Title Page

Item (73), Assignee should read as follows:
Cook Medical Technologies, LLC
Bloomington, IN (US)

Signed and Sealed this
Seventeenth Day of September, 2024

Katherine Kelly Vidal
*Director of the United States Patent and Trademark Office*